(12) United States Patent
Glenn, Jr. et al.

(10) Patent No.: US 6,989,149 B2
(45) Date of Patent: Jan. 24, 2006

(54) DELIVERY OF REACTIVE AGENTS VIA SELF EMULSIFICATION FOR USE IN SHELF-STABLE PRODUCTS

(76) Inventors: Robert Wayne Glenn, Jr., Truscott, Knowle Hill, Virginia Water, Surrey, GU25 4HZ (GB); James Charles Dunbar, 14 Midway, Walton-On-Thames, Surrey KT12 3HZ (GB); Tharwat Tadros, 89 Nash Grove Lane, Wokingham, Berkshire RG40-4HE (GB)

( * ) Notice: Subject to any disclaimer, the term of this patent is extended or adjusted under 35 U.S.C. 154(b) by 0 days.

(21) Appl. No.: 09/764,561

(22) Filed: Jan. 17, 2001

(65) Prior Publication Data

US 2002/0131945 A1 Sep. 19, 2002

(51) Int. Cl.
*A61K 6/00* (2006.01)
*A61K 7/06* (2006.01)

(52) U.S. Cl. .................. 424/401; 424/70.1; 424/70.11

(58) Field of Classification Search ............... 424/70.1, 424/70.11, 401
See application file for complete search history.

(56) References Cited

U.S. PATENT DOCUMENTS

| | | | |
|---|---|---|---|
| 3,484,417 A | 12/1969 | Kalopissis et al. | |
| 3,549,602 A | 12/1970 | Kalopissis et al. | |
| 4,102,641 A | 7/1978 | Tuffile et al. | |
| 4,567,039 A | 1/1986 | Stadnick et al. | |
| 4,973,475 A | 11/1990 | Schnetzinger et al. | |
| 5,030,756 A | 7/1991 | Deppert et al. | |
| 5,087,733 A * | 2/1992 | Deppert et al. | |
| 5,206,013 A | 4/1993 | Deppert et al. | |
| 5,211,942 A | 5/1993 | Deppert et al. | |
| 5,254,335 A | 10/1993 | Deppert et al. | |
| 5,350,572 A | 9/1994 | Savaides et al. | |
| 5,523,080 A | 6/1996 | Gough et al. | |
| 5,525,332 A * | 6/1996 | Gough et al. | |
| 5,935,560 A | 8/1999 | Seper et al. | |

FOREIGN PATENT DOCUMENTS

| | | |
|---|---|---|
| CA | 2024509 AA | 2/1992 |
| EP | 0 159 628 | 10/1985 |
| EP | 0 437 099 A1 | 7/1991 |
| GB | 2197887 A | 6/1988 |
| WO | WO 94/26237 | 11/1994 |
| WO | WO 96/03966 | 2/1996 |
| WO | WO 98/38974 | 9/1998 |
| WO | WO 00/040209 A2 | 7/2000 |
| WO | WO 00/040210 A2 | 7/2000 |

OTHER PUBLICATIONS

M.J. Rang, C.A. Miller "Spontaneous emulsification of oil drops containing surfactants and medium-chain alcohols", Progr Colloid Polym Sci (emulsions and microemulsions) 1998, 101-117, vol. 108, Steinkopff Verlag.

* cited by examiner

Primary Examiner—Thurman K. Page
Assistant Examiner—Humera N. Sheikh
(74) Attorney, Agent, or Firm—Linda M. Sivik; Tara M. Rosnell

(57) ABSTRACT

Disclosed are treatment compositions comprising a liquid emulsifiable concentrate which comprises a chemically unstable reactive agent wherein the reactive agent is comprised of one or more reactive groups of the electrophilic, nucleophilic or protected thiol type, a water immiscible solvent, one or more surfactants, which is usable upon dilution within a separate aqueous composition to form a micro- or macro-emulsion in-situ immediately prior or simultaneous to application to the substrate and wherein the reactive agent is chemically shelf stable. Also disclosed are methods for treating amino acid based substrates, and methods for bleaching, coloring and conditioning hair with these treatment compositions.

18 Claims, No Drawings

DELIVERY OF REACTIVE AGENTS VIA SELF EMULSIFICATION FOR USE IN SHELF-STABLE PRODUCTS

TECHNICAL FIELD

The present invention relates to a system for the delivery of reactive cosmetic actives (such as reactive conditioners, dyes, styling aids, sunscreens etc.) to amino acid based substrates from a chemically shelf stable formulation in a manner which is aesthetically acceptable to consumers.

BACKGROUND OF THE INVENTION

Consumers have been treating amino acid based substrates for years. Such treatments have included the waterproofing or coloring of textiles, the sunscreening of skin, the coloring, conditioning, and styling of hair, the dentifrice treatment of teeth, and more. It is well known that if such treatments can be done by safe covalent attachment to the substrate, that the treatment will be much more long lasting. Therefore, several reactive chemistries have been developed to provide covalent attachment to amino acid based substrates such as hair. Historically, these technologies, based on covalent attachment of cosmetic actives, have primarily relied upon electrophilic (electron accepting) and nucleophilic (electron donating) reactive groups or "hooks". (Please see WO98/38974 by G. Malle et. al., U.S. Pat. No. 5,935,560 by J. Seper et. al., U.S. Pat. No. 5,525,332 by A. Gough et. al., WO96/03966 by P. Baile et. al., U.S. Pat. No. 5,523,080 by A. Gough et. al., WO94/26237 by A. Gough et. al., U.S. Pat. No. 5350572 by A. Savaides et. al., U.S. Pat. No. 5,254,335 by T. Deppert et. al., U.S. Pat. No. 5,206,013 by T. Deppert et. al., U.S. Pat. No. 5,211,942 by T. Deppert et. al., EP0 437099A1 by D. Halloran et. al., CA 2024509AA by B. Murphy et. al., U.S. Pat. No. 5,087,733 by T. Deppert et. al., U.S. Pat. No. 5,030,756 by T. Deppert et. al., U.S. Pat. No. 4,973,475 by R. Schnetzinger et. al., GB 2197887A by C. Mahieu et. al., U.S. Pat. No. 4,567,039 by R. Stadnick et. al., EP0 159628 by R. Stadnick et. al., U.S. Pat. No. 4,102,641 by A. Cunningham et. al., U.S. Pat. No. 3,549,602 by G. Kalopissis et. al., U.S. Pat. No. 3,484,417 by G. Kalopissis et. al.) More recently, a Protected Thiols "hook" technology for the covalent attachment of cosmetic actives to amino acid substrates has been proposed. (Please reference WO2000040210A2 by R. Glenn et. al., and WO2000040209A2 by R. Glenn.)

It is highly desirable to formulate and apply hair care products as aqueous solutions or aqueous emulsions for a number of consumer preferred attributes. Aqueous solutions provide superior ease of rinsing, hair feel, less coating of bathroom tiles, etc. than oil based compositions. However, attaining such aqueous compositions is problematic. The reactive groups or "hook" moieties which are reactive towards amino acid residues, are also reactive towards electron rich ingredients that are employed in the formulation of consumer products to deliver these actives, including water and even atmospheric oxygen. This leads to premature decomposition of the "hooks" compounds, referred to herein as reactive agents, over the shelf life of the product which severely or completely mitigates reactive efficacy with hair upon usage by the consumer.

The primary advantage of this invention is the discovery of a delivery system approach that will enable the treatment of reactive agents to hair from a 1) chemically shelf stable composition that is 2) applied to hair in a consumer desired product form, e.g., as an aqueous emulsion.

This is accomplished via a self-emulsifying hair delivery system comprising a separately packaged liquid emulsifiable concentrate that is essentially non-aqueous, comprising the reactive agent, that is able to self or spontaneously emulsify upon dilution with water or a separate aqueous composition. Such dilution may be done by the consumer, to form an aqueous micro- or macro-emulsion with minimal or no agitation either immediately prior to or simultaneous to application to hair. While not being bound by theory, such low energy emulsification with minimal or no agitation by the consumer, e.g., by soft shaking of bottle or suitable container, is achieved via inclusion of specialized surfactants and/or dispersing aides within the liquid concentrate that achieve either ultra-low interfacial tension and/or substantial interfacial disruption between the liquid concentrate and the aqueous phase upon dilution with water or a separately packaged aqueous composition.

Surprisingly, it has been discovered that the liquid emulsifiable concentrates of the present invention can achieve self emulsification even upon addition to a substantially thickened aqueous composition to produce a resulting homogenous and viscous emulsion with minimal agitation by the consumer, e.g., via gentle shaking of the bottle or suitable container container. This is in marked contrast to conventional thickened emulsions which necessitate considerable energy input that can only be attained by employing high energy processing equipment within a laboratory or a manufacturing plant, e.g., a lightning mixer or agitated vessel. Accordingly, the liquid emulsifiable concentrates of the present invention enable isolation upon storage for acceptable chemical shelf stability while still enabling emulsion delivery with minimal inconvenience to the consumer.

SUMMARY OF THE INVENTION

This invention relates to treatment compositions comprising a liquid emulsifiable concentrate which comprises a chemically unstable reactive agent, a water immiscible solvent, one or more surfactants, and, optionally a dispersing aide, which is usable upon dilution within a separate aqueous composition to form a micro- or macro-emulsion in-situ immediately prior or simultaneous to application to the substrate.

DETAILED DESCRIPTION OF THE INVENTION

The present invention relates to delivery of chemically unstable reactive agents via liquid emulsifiable concentrates for use in chemically shelf stable products.

The term "amino acid based substrates", as used herein, refers to proteinaceous materials, such as keratin, as found in human and animal hair, skin, and nails.

The term "covalently reactive", as used herein, refers to the ability of reactive agents to form covalent bonds with functional groups within proteinaceous keratin, e.g., with keratin amino acids comprising —SH, —OH, —NH$_2$ or —S—S— groups, thereby forming a permanent bond with the keratin that is resistant to shampooing or cleansing.

The term "water immiscible solvent", as used herein, refers to solvents having a maximum solubility in water of less than 10%.

The term "reactive agent", as used herein, refers to compounds that comprise a reactive group or "hook" that is covalently reactive with keratin and a mono or multivalent cosmetically active functional group that imparts one or more visual, tactile or other cosmetic beneficial effects on proteinaceous materials such as keratin, i.e., hair, skin, animal fur or wool.

The term "chemically shelf stable" or "chemically stable", as used herein, applies to a composition comprising a reactive agent wherein the reactive agent does not chemically decompose substantially (via hydrolysis, reduction or oxidation) over the desired shelf life of the product such that the reactive agent maintains its efficacy to deliver the desired benefits unto the proteinaceous substrate.

The treatment compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

It is highly desirable to formulate reactive agents within aqueous systems for a number of consumer desired attributes, e.g., hair feel, ease of rinsing, less coating of bathroom tiles etc. This poses a major dilemma for emulsions comprising reactive agents, as these 'reactive' compounds are generally too chemically unstable to be stored within an aqueous environment over the required shelf life of the product.

One means that has been identified that will enable the treatment of reactive agents to hair from a 1) chemically shelf stable composition that that 2) can be applied by the consumer to the hair in a desirable product form, e.g., as an oil-in-water emulsion, is achieved by formulating the reactive agent within an anhydrous formulation, using an organic solvent that is water miscible, which can be admixed by the consumer with a separate aqueous composition immediately prior to application to the hair substrate to produce an oil-in-water emulsion. The reactive agent would retain its chemical stability within the anhydrous formulation during the shelf life of the product.

In practice, to produce an oil-in-water emulsion, vigorous mixing is required to obtain the desirable emulsion homogeneity and droplet sizes for good performance. Such vigorous mixing is conventionally applied via mechanical mixing within an equipped laboratory, pilot plant or manufacturing plant, e.g., overhead mixers, static mixers, high shear mixers, homogenizers, blenders etc. Accordingly, emulsions that exist within cosmetic products must generally be produced at the point of manufacture, e.g., in a manufacturing plant or laboratory, prior to shipment to the shelves with the resulting emulsion having to be shipped and shelved for many months if not greater than a year prior to use by the consumer.

It has been discovered that the above mentioned 'mixing' dilemma can be solved via a self-emulsifying hair delivery system comprising a separately packaged liquid emulsifiable concentrate comprising the reactive agent that is able to self or spontaneously emulsify upon dilution with water, or separate aqueous composition, by the consumer to form an aqueous micro- or macro-emulsion with minimal or no agitation, i.e., self or spontaneous emulsification, either immediately prior to or simultaneous to application to hair. While not being bound to theory, such low energy emulsification with minimal or no agitation by the consumer, e.g., by soft shaking of bottle or suitable container, is achieved via inclusion of specialized surfactants and/or dispersing aides within the liquid concentrate that achieve either ultra-low interfacial tension and/or interfacial turbulence between the oil and the aqueous phase upon dilution with water or a separately packaged aqueous composition. Alternatively, self emulsification can be enhanced with dispersing aides such as hydrophilic silica or medium chain alcohols, which on transport from the oil to the aqueous phase will induce additional interfacial turbulence.

The term spontaneous emulsification is usually limited to situations where no external energy of agitation is supplied. Self emulsification generally refers to situations where a small amount of energy is supplied to achieve gentle mixing. An extensive literature exists on spontaneous emulsification and various mechanisms have been suggested [See Progr Colloid Poly Sci (1998) 109:101–117 by M. J. Rang and C. A. Miller]. Self emulsification of an oil phase in water is of interest, for example, in the use of emulsifiable concentrates of agricultural chemicals and more recently for drug delivery [See WO9848624 by K. Narayanan et. al., U.S. Pat. No. 6,033,681 by K. Narayanan et. al., and Advanced Drug Delivery Reviews, 25 (1997) 47–58 by C. W. Pouton]. A suitable surfactant or surfactant mixture is added to an oil phase containing a pesticide or drug to enable it to disperse and emulsify when added to water under conditions where gentle mixing occurs. For agricultural chemicals and pharmaceuticals, the emulsification is generally attained via dilution with non-viscous water, e.g., diluted with water by a farmer to form an emulsion of the pesticide for efficient transport to crops or with water within the gut to form a fine emulsion thereby improving bioavailability of the drug active.

Surprisingly, it has been discovered that the liquid emulsifiable concentrates of the present invention can achieve self emulsification even upon dilution with substantially thickened aqueous compositions (vs. conventional water) to produce a resulting homogenous and viscous emulsion with minimal agitation by the consumer, e.g., via gentle shaking of the bottle or suitable container container. Accordingly, it has been discovered that the liquid emulsifiable concentrates of the present invention can be delivered across a myriad of consumer acceptable cosmetic product forms including, but not limited to, moderate to high viscosity liquids, lotions, dispersions, gels, and creams. Such a discovery enables delivery of the liquid emulsifiable concentrates of the present invention with non-drip aqueous compositions including hair shampoos, skin cleansers, skin lotions, hair conditioners, hair dyes, hair permanent waves, hair straighteners, hair bleaches, styling sprays, hair mousses, two-in-one shampoos, fabric softeners, lotions, nail polishes, hair serums, hair dyes, hair waving, etc.

Reactive Component

The compositions of the present invention comprise a reactive component which in turn comprises a chemically unstable reactive agent that is incorporated within a water immiscible solvent. The reactive agent comprises a reactive group or "hook" and a mono or multivalent cosmetically active functional group that imparts one or more visual, tactile or other cosmetic beneficial effects on proteinaceous materials such as keratin, i.e., hair, skin, animal fur or wool.

Disclosed technologies for the covalent attachment of cosmetic actives (primarily dyes and conditioners) to hair keratin have primarily relied upon electrophilic (electron accepting) and nucleophilic (electron donating) reactive groups or "hooks". Also disclosed are Protected Thiols reactive "hooks" for the covalent modification of hair keratin.

Electrophilic reactive groups or "hooks" that may be included within reactive agents of the present inventions include, but are not limited to, the following:

Azlactones as described in U.S. Pat. No. 5,656,265 by P. Bailey et. al., and U.S. Pat. Nos. 5,523,080, 5,525,332 both by A. Gough et. al., and all incorporated by reference, Alkyl halides as described in U.S. Pat. Nos. 5,211,942 and 5,030,756 by T. Deppert et. al., both incorporated by reference, Thiosulfates as described in U.S. Pat. No. 3,415,606 by R. Randebrock and incorporated by reference, Acyl halides, polyhaloacetylated polymers are essentially characterized in that they all contain a halogen (chlorine or bromine, but preferably chlorine) on a carbon in the alpha position relative to a carbonyl group. These polymers which are polyhaloacetylated and preferably polychloroacetylated, may be obtained according to different methods. In particular, they may be obtained by the homopolymerization or the copolymerization of a haloacetylated monomer carrying a polymerizable double bond; among the haloacetylated monomers, there will be mentioned, in particular, the following: vinyl chloroacetate, allyl chloroacetate, vinyl chloroformate, N-allyl chloroaceta-methyl 2-chloroacetamidoacrylate, N-chloroacetamidomethyl acrylamide, N-chloroacetamidomethyl methacrylamide, 5 2-(chloroacetoxy)propyl methacrylate, 2-(chloroacetylcarbamoyloxy)propyl methacrylate, N-methacryloyl-N'-chloroacetylurea and the Like; in the case of a copolymerization, a comonomer which promotes the solubility of the final copolymer in the solvent desired, which is generally water or a water-alcohol mixture, is preferably chosen; among comonomers, there will be mentioned, in particular, the following N-vinylpyrrolidone, N,N-dimethylacrylamide,N-acrylamidomethyl-2-oxopyrrolidone, 3-methacrylamidopropyl-1(N,N,N-trimethylammonium) chloride, methylacrylate, methylmethacrylate, N,N-dimethylacrylamide and the like. The haloacetylated monomers are known and may be prepared according to known methods. The polyhaloacetylated polymers may also be obtained by attaching a haloacetyl group to a polymer carrying amine or primary or secondary alcohol groups, the haloacetyl group being attached in a known manner which consists in reacting a haloacetyl halide, preferably chloroacetyl chloride, with the said polymer carrying amine or alcohol groups; among the polymers which nay be employed for this haloacetylation reaction, there may by mentioned, in particular: polyvinyl amine, polyvinyl alcohol, 2-hydroxyethyl polyacrylate, polylysine, copolymers obtained by condensing 2,2-dimethyl-1,3-diaminopropane with methylene bisacrylamide, water-soluble protein hydrolysates and the like. The polyhaloacetylated polymers employed preferably have a molecular weight generally of between 500 and 50,000. Although some of the homopolymers and copolymers are known, examples for the preparation of some of them as well as examples for the preparation of the haloacetylated monomers will be given as follows: Among the homopolymers and the polyhaloactylated-copolymers which are particularly preferred for implementing the method, the following may be mentioned: N-vinylpyrrolidone/vinyl chloroacetate copolymer, methyl 2-chloroacetamidoacrylate/N-acrylamido-methyl-2-oxopyrrolidine copolymer, methyl 2-chloroacetamidoacrylate homopolymer, N-chloroacetamidomethyl acrylamide/N-acrylamidomethyl-2-oxopyrrolidine copolymer, methyl 2-chloroacetamidoacrylate/methacrylamido-propyl trimethylammonium chloride copolymer, N-chloroacetamidomethyl acrylamide/methyl acrylate copolymer, N-chloroacetamidomethyl acrylamide homopolymer, and N-chloroacetamidomethyl acrylamide/methacrylamido-propyl trimethylammonium chloride copolymer.

Dithiocarboxylic acid esters, wherein preferred carboxyalkyl carbodithioates have the general formula:

where R is an organic group and

R$^1$ is an alkylene group containing 1, 2 or 3 carbon atoms.

The group R may be:
(a) an aliphatic group, for example alkyl, which may contain for instance up to 24 carbon atoms;
(b) an aromatic group, for example phenyl and naphtyl;
(c) a mixed aliphatic-aromatic group, for example alkaryl or aralkyl;
(d) a heterocyclic group, for example furyl;
(e) a quaternary ammonium-alkylene group, for example an N-pyridinium-alkylene group;
(f) a chromophoric group, for example anthraquinonyl, an azo-containing radical, phthalocyanine; or
(g) any group (a) to (e) containing substituents such as carboxyl, sulphonic acid, halogeno, nitro, oxo, hydroxyl, acylamino, or a further carboxyalkyl carbodithioate group, but not mercapro (—SH) or primary amino (—NH$_2$).

N-ethylmaleimides

Halotriazines and halopyrimidines as described U.S. Pat. No. 3,340,000 by A. Shansky and incorporated by reference, Vinylsulfones as manufactured by Carbic Hoechst Corporation, 451 Washington Street, New York 13, N.Y. The structural formula for a typical vinyl sulfone is the following:

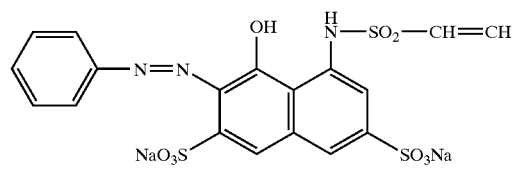

A list of vinyl sulfones includes: Remazol Red (B), Remazol Black (B), Remazol Brilliant Blue (R), Remazol Red-Violet (R), Remazol Yellow (RT) and Remazol Yellow (GN).

Urea derivatives as described in U.S. Pat. No. 3,725,525 by B. Joos, and incorporated by reference Alkoxysilanes U.S. Pat. No. 4,567,039 by R. Stadnick et. al. and incorporated by reference, Isothiuroniums as described in U.S. Pat. No. 5,254,335 by T. Deppert et. al. and U.S. Pat. No. 5,206,013 by T. Deppert et. al., both incorporated by reference, and Monohalotriazines and dihalotriazines, dihaloquinoxaline, dihalopyrimidines, β-haloethylsulfones, β-sulfatoethylsulfones, acrylates, methacrylates, acrylamides, methacrylamides, malemimides, halomaleimides, epoxides, aziridines and derivatives, esters, oxazolinium, imidazolium, thiazolidinium, acid derivatives of carboxylates and sulfates, esters, carbamates, anhydrides, isothiocyanates, isocyanates, lactones, and azalactones having the structure:

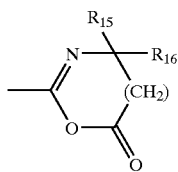

wherein Z represents the remainder of the molecule, $R_{15}$ and $R_{16}$ can be the same or different chosen from $C_1$–$C_{12}$ alkyl, $C_2$–$C_{24}$ alkenyl, $C_3$–$C_{12}$ cycloalkyl, $C_5$–$C_{26}$ aryl or $R_{15}$ and $R_{16}$ can form a carbocyclic containing 4 to 12 atoms and further wherein any $R_{15}$ and $R_{16}$ can contain 0 to 3 heteroatoms chosen from S, N, and O.

Nucleophilic reactive groups or "hooks" that may be included within reactive agents of the present inventions include, but are not limited to, the following:

thiols or thiolates as described in U.S. Pat. No. 3,484,417 by G. Kalopissis et. al., U.S. Pat. No. 5,935,560 by J. Seper et. al., U.S. Pat. No. 5,776,454 (Gee et al.), and U.S. Pat. No. 5,935,560 by J. Seper et. al., all incorporated by reference, thiols or thiolates containing quaternary salts as described in U.S. Pat. No. 4,973,475 by R. Schnetzinger et. al., U.S. Pat. No. 5,087,733 by T. Deppert et. al., U.S. Pat. No. 5,206,013 by T. Deppert et. al., all incorporated by reference, thioalkylamides as described in U.S. Pat. No. 5,068,378 by D. Halloran et. al., incorporated by reference, thioalkyl esters as described in U.S. Pat. No. 5,350,572 by A. Savaides et. al., incorporated by reference and cysteamine derivatives having the formula:

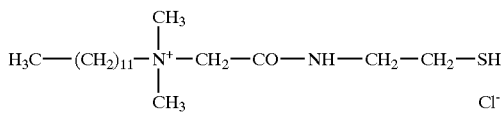

wherein the above formula is N-dodecyl-N,N-dimethyl glycine cysteamine hydrochloride, also known as N-dodecyl amino betaine mercaptoethylamine (DABM).

Protected Thiol reactive groups or "hooks" that may be included within reactive agents of the present inventions include, but are not limited to, reactive groups of the following structure:

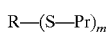

where R is a mono or multivalent cosmetically active functional group, S is sulfur, Pr is a protecting group and m is an integer between 1 and 100. The protecting group is selected from the group consisting of heterocyclic protecting groups, $sp^2$ aliphatic trigonal carbon protecting groups, $sp^3$ carbon electrophilic protecting groups, phosphorus protecting groups, metal based protecting groups, non-metal and metalloid based protecting groups, energy-sensitive protecting groups and mixtures thereof as described in pending U.S. application Ser. No. 09/478,855 by R. Glenn et. al. and pending U.S. application Ser. No. 09/227,912 by R. Glenn, both of which are incorporated herein.

Preferred reactive groups or "hooks" of the present invention include those of the Protected Thiol type. Of the thiol protective groups, the heterocyclic protecting groups, the $sp^2$ protecting groups and the phosphorus protecting groups are preferred, with the heterocyclic protecting groups being more preferred. Of the heterocyclic protecting groups, the pyrimidinium, pyridinium, and benzothiazolium classes are preferred, with the pyrimidinium class being more preferred.

The mono or multivalent cosmetically active functional group, R, suitable for inclusion within the reactive agents of the present invention may be any moiety that imparts one or more visual, tactile or other cosmetic beneficial effects on proteinaceous materials such as keratin, i.e., hair, skin, animal fur or wool. Any cosmetic moiety may be included as a functional group in the compositions of the present invention as long as the compound can be modified to contain at least one reactive group or "hook" as described herein and in the references provided herein.

Suitable functional groups that are suitable for inclusion within the reactive agents of the present invention include, but are not limited to, antimicrobial compounds, UV-absorbing compounds, skin conditioning agents, hair conditioning agents, hair repair agents, hair styling agents, hair dyes, scalp treatment agents, anti-inflammatory compounds, antioxidants, dyes and coloring agents, perfumes, oral care actives, skin moisturizers, pharmaceutical agents, antidandruff agents, insect repellents, moisturizers, humectants, pearlescent and/or opacifying materials, fabric care actives, pet grooming actives, fabric anti-wrinkling agents, shrink-resistant actives, laundry care actives, hard surfaces actives, textile actives, textile dyes, water-proofing agents, cationic polymers, cationic surface modifiers, hydrophobic surface modifiers, anionic surface modifiers, absorbents, antifungal agents, insecticidal agents, textile color guards, nail actives such as enamel and polish, eyelash actives and mascara, antiperspirant and deodorant actives, anti-acne actives, odor control actives, fluorescent actives, bleaching agents, enzymes, antibodies, dispersing aids, emollients, stabilizers, anti-static agents, anti-seborrhea agents, optical brighteners, fluorescent dyes, softeners, cross-linking agents, photobleaches, bactericides, and mixtures thereof and as further described in pending U.S. application Ser. No. 09/478,855 by R. Glenn et. al. which is herein incorporated by reference.

Preferred cosmetic functional groups include hair conditioning agents, hair repair agents, hair styling agents, and hair dyes and coloring agents as further described in pending U.S. application Ser. No. 09/478,855 by R. Glenn et. al. which provides a more thorough list of preferred cosmetic functional groups and is incorporated by reference herein.

An exemplary reactive agent to demonstrate the present invention comprises a Protected Thiol reactive group of the pyrimidinium type combined with a silicone hair conditioning cosmetic functional group. The structure of this exemplary reactive agent is as follows:

Polymer I

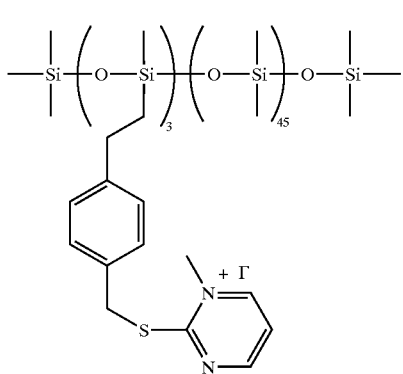

This compound and its synthesis preparation are disclosed within U.S. application Ser. No. 09/478,855 by R. Glenn et. al. which is incorporated by reference herein. Additional reactive agents containing a silicone hair conditioning cosmetic functional group are be found within U.S. application Ser. No. 09/616,535 by M. Butts et al., filed Jul. 14, 2000, U.S. application Ser. No. 09/616,534 by M. Butts et al., filed Jul. 14, 2000, U.S. application Ser. No. 09/616,533 by M. Butts et al., filed Jul. 14, 2000, U.S. application Ser. No. 09/616,532 by M. Butts et al., filed Jul. 14, 2000, all of which are incorporated by reference herein. Polymer I is chemically shelf unstable with the pyrimidinium moiety being prone to premature hydrolysis in the presence of aqueous media.

An additional exemplary reactive agent to demonstrate the present invention comprises an electrophilic reactive group of the azlactone type combined with a silicone hair conditioning cosmetic functional group. The structure of this exemplary reactive agent is as follows:

Polymer II

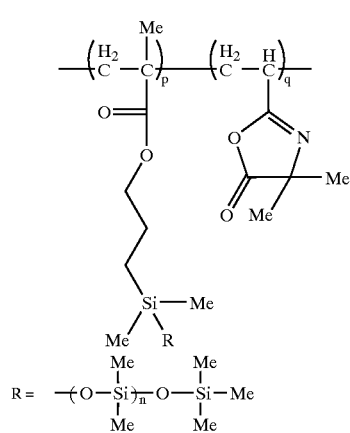

where p=1, q=14.6 and n=60. This compound and its synthesis preparation is disclosed within U.S. Pat. No. 5,525,332 by A. D. Gough et. al. from column 12, lines 11–67 through Column 13, lines 1–18.

An additional exemplary reactive agent to demonstrate the present invention comprises a nucleophilic reactive group of the thiol type combined with a hydrocarbon conditioning cosmetic functional group. The structure of this exemplary reactive agent is as follows:

Conditioner III

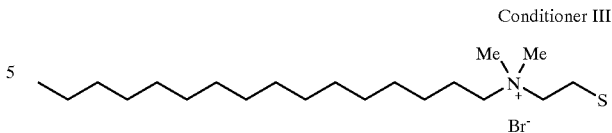

This compound and its synthesis preparation is disclosed within U.S. Pat. No. 5,087,733 by T. M. Deppert et. al. from column 6, lines 35–68 and Column 7, lines 10–15, which is herein incorporated by reference.

Water Immiscible Solvent

The water immiscible solvent include, but are not limited to, the group consisting of vegetable oil, castor oil, petroleum distillates, hydrocarbon compounds, silicone compounds, esters of $C_6$–$C_{18}$ alkyl acetates, esters of $C_1$–$C_4$ carboxylic acid and $C_6$–$C_{18}$ alcohols, $C_6$–$C_{18}$ alkyl carbonates, $C_6$–$C_{18}$ diols, sterically hindered $C_6$–$C_{18}$ N-alkyl pyrrolidones and $\alpha$-$C_1$–$C_4$ alkyl derivatives thereof, and mixtures thereof.

The water immiscible solvent can a volatile or nonvolatile silicone compound, a volatile or nonvolatile hydrocarbon compound, or mixtures thereof. The volatile silicone compounds can be a linear or cyclic polydimethylsiloxane, such as hexamethylsiloxane or a cyclomethicone, available commercially under the trade names such as DOW CORNING 200 FLUID, DOW CORNING 244 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y.

Volatile hydrocarbon compounds include hydrocarbons having about 10 to about 30 carbon atoms, for example, isododecane and isohexadecane, i.e., PERMETHYL 99A, PERMETHYL 101A, and PERMETHYL 102A, available from Presperse, Inc., South Plainfield, N.J. The volatile hydrocarbon compounds can also include aliphatic hydrocarbon having about 12 to about 24 carbon atoms, and having a boiling point of about 90° C. to about 250° C., i.e., ISOPAR C, ISOPAR E, ISOPAR G, and ISOPAR M, available from Exxon Chemical Co., Baytown, Tex. Other exemplary volatile hydrocarbon compounds are depicted in general structure (I):

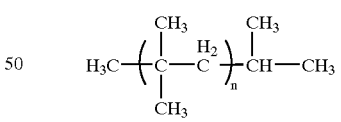

where n ranges from 2 to 5.

Additional water immiscible solvents include propylene carbonate, available commercially as ARCONATE PROPYLENE CARBONATE, available from ARCO Chemical Company, and hydrofluoroethers, available commercially as HFE-7100, HFE-71 DE, HFE-71 DA, HFE-71IPA, and HFE-7200, available from 3M Chemicals.

Nonvolatile water immiscible hydrocarbon solvents include mineral oil, a pheyltrimethicone, isopropyl myristate, castor oil, or branched hydrocarbons according to structure I where n is 5–250 including PERMETHYL 104A, PERMETHYL 106A, and PERMETHYL 108A, available from Presperse, Inc., South Plainfield, N.J. Nonvolatile water immiscible solvents also include polydimethylsiloxanes having a viscosity at 25° C. of about 6 to about 400 centistokes, such as DOW CORNING 556 FLUID, or DOW CORNING 200 FLUID, respectively, available from Dow Coming Corp., Midland, Mich.

Other water immiscible solvents that can be incorporated into the compositions include, but are not limited to, branched 1-decene oligomers, like 1-decene dimer or polydecene; and esters having at least about 10 carbon atoms, and preferably about 10 to about 32 carbon atoms. Suitable esters include those comprising an aliphatic alcohol having about eight to about twenty carbon atoms, and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Preferably, the ester has a molecular weight of less than about 500. Suitable esters include, but are not limited to, a) aliphatic monohydric alcohol esters, including, but not limited to, myristyl propionate, isopropyl isostearate, isopropyl myristate, isopropyl palmitate, cetyl acetate, cetyl propionate, cetyl stearate, isodecyl neopentonoate, cetyl octanoate, isocetyl stearate; b) aliphatic di- and tri-esters of polycarboxylic acids, including, but not limited to, diisopropyl adipate, diisostearyl fumarate, dioctyl adipate, and triisostearyl citrate; c) aliphatic polyhydric alcohol esters, including, but not limited to, propylene glycol dipelargonate; d) aliphatic esters of aromatic acids, including, but not limited to $C_{12}$–$C_{15}$ alcohol esters of benzoic acid, octyl salicylate, sucrose benzoate, and dioctyl phthalate. Numerous other esters are listed in the International Cosmetic Ingredient Dictionary and Handbook, Vol. 2, Eight Ed., The Cosmetic Toiletry and Fragrance Assn., Inc., Washington, D.C. (2000) at pages 1670 through 1676, incorporated herein by reference.

The water immiscible solvent may be a di- or tri-glyceride. Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Preferred water immiscible solvents for use in the present invention include
volatile hydrocarbon compounds having about 12 to about 24 carbon atoms, and having a boiling point of about 90° C. to about 250° C., i.e., ISOPAR C, ISOPAR E, ISOPAR G, and ISOPAR M, available from Exxon Chemical Co., Baytown, Tex.;
volatile silicone compounds such as hexamethylsiloxane or a cyclomethicone, available commercially under the trade names such as DOW CORNING 200 FLUID, DOW CORNING 244 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y.; and
propylene carbonate, available commercially as ARCONATE PROPYLENE CARBONATE, available from ARCO Chemical Company.
The solvent selected must be able to dissolve or disperse the polymer. In the case where the polymer is not fully soluble in the solvent, the partial solution or dispersion is such that the system is physically stable. That is, the dispersion does not settle out, or separate into more than one phase, over time. Such solutions or dispersions are often clear, but may be turbid or cloudy.

The water immiscible solvent comprises from about 1% to about 50%, more preferably from about 2% to about 40%, and most preferably from about 3% to about 30% by weight of the composition.

Surfactants

Suitable surfactants for inclusion within the liquid emulsifiable concentrates of the present invention include cationic, anionic, nonionic, amphoteric, zwitterionic surfactants and Gemini surfactants.

Examples of suitable cationic surfactants include quaternary ammonium salts, e.g., tetramethylammonium halides, alkyltrimethylammonium halides in which the alkyl group has from about 8 to 22 carbon atoms, for example octyltrimethylammonium chloride, dodecyltrimethylammonium chloride, hexadecyltrimethylammonium chloride, cetyltrimethylammonium chloride, and behenyltrimethylammonium chloride, benzyltrimethylammonium chloride, octyldimethylbenzyl-ammonium chloride, decetyldimethylbenzylammonium chloride, stearyldimethylbenzylammonium chloride, distearyldimethylammonium chloride, didodecyldimethylammonium chloride, dioctadecyldimethylammonium chloride, tallow trimethylammonium chloride, cocotrimethylammonium chloride, cetylpyridinium chloride and the other corresponding halides and hydroxides.

Non-ionic surfactants suitable for use in the compositions of the present invention include condensation products of aliphatic ($C_8$ to $C_{18}$) primary or secondary linear or branched chain alcohols or phenols with alkylene oxides, usually ethylene oxide, and generally having from 1 to 30 ethylene oxide groups.

Other suitable non-ionic surfactants include mono- or di-alkyl alkanolamides. Examples include coco mono- or di-ethanolamide or coco-isopropanolamide. Further suitable nonionic surfactants are the alkyl polyglycosides (APG's). Typically, the APG is one which comprises an alkyl group connected (optionally via a bridging group) to a block of one or more glycosyl groups. Preferred APG's are described by the following formula:

RO—(G)$_n$ wherein R is a branched or straight chain alkyl group which may be saturated or unsaturated, and G is a saccharide group. R may represent a man alkyl chain length from about $C_5$ to about $C_{20}$. G may be selected from the group comprising glucose, xylose, fructose, mannose and derivatives thereof. Preferably, G is glucose. The degree of polymerization, n, may have a value of from about 1 to about 10 or more.

Esters of polyols and sugars, the polyethoxylated and/or polypropoxylated alkylphenols, the polyhydroxylated polyethers of fatty alcohols, fatty acid alkanolamides, amine oxides, and the condensation products of ethylene oxide with long chain amides are also representative of suitable nonionic surfactants.

Other types of nonionics may include propylene oxide and ethylene oxide condensates, for example the Pluronic series produced by BASF.

Amphoteric and zwitterionic surfactants suitable for use in compositions of the invention may include alkyl amine oxides, alkyl betaines, alkyl amidopropyl betaines, alkyl sulfobetaines, alkyl glycinates, alkyl carboxyglycinates, alkyl amphopropionates, alkulamphoglycinates, alkyl amidopropyl hydroxy-sultaines, acyl taurates and acyl glutamates, wherein the alkyl and acyl groups have from abut 8 to 19 carbon atoms. Examples include lauryl amine oxide, cocodimethyl sulphopropyl betaine and preferably lauryl betaine, cocamidopropyl betaine and sodium cocamphoproprionate.

Suitable anionic surfactants are the alkyl sulfonates, alkyl ether sulfonates, alkylaryl sulfonates, alkanoyl isethionates, alkyl succinates, alkyl sulfosuccinates, N-alkoyl sarcosinates, alkyl phosphates, alkyl ether phosphates, alkyl ether carboxylates, and alpha-olefin sulfonates, especially their sodium, magnesium, ammonium and mono-, di- and triethanolamine salts. The alkyl and acyl groups generally contain from 8 to 18 carbon atoms and may be unsaturated. The alkyl ether sulfates, alkyl ether phosphates and alkyl ether carboxylates may contain from one to 10 ethylene oxide or propylene oxide units per molecule.

Optional surfactants which may be included are fatty alcohols or fatty acids, or derivatives thereof, or a mixture of any of these, having a chain length of from about 8 to about 28 carbon atoms, preferably from about 12 to 18 carbon atoms. These materials may be predominantly linear or may be branched.

Other amphoterics may be those of the dialkyl type including either phospholipids, i.e., based on glycerol and sphingosine, or glycolipid, i.e. based on sphingosine. Phospholipids are preferred with phosphatidyl choline (lecithin) being the preferred phospholipid. Of the alcohol moieties which comprise the phosphoglycerides, serine, choline and ethanolamine are particularly preferred, and of the fatty chains, those having a chain length of $C_{14}$ to $C_{24}$ are preferred. The fatty acid chains may be branched or unbranched, saturated or unsaturated, and palmitic, myristic, oleic, stearic, arachidonic, linolenic, linoleic and arachidic acids are particularly preferred.

Preferred nonionic surfactants include, but are not limited to, ethoxylated and polyethoxylated alcohols, ethoxylated alkyl phenols, linear aliphatic polyesters, linear aromatic polyesters, linear aliphatic ethoxylates, branched aliphatic ethoxylates, polyethoxylated castor oil, polyethoxylated carboxylates, and polyethoxylated alkylamines. Preferred anionic surfactants include phosphate esters, and their salts, alkyl sulfonamides, alkyl sulfosuccinates, salts of sulfated nonylphenoxylpoly(ethyleneoxy) ethanol, salts of alkylbenzene sulfonates, salts of alkylnaphthalene sulfonate, and sulfonated aliphatic polyesters and their salts.

Specific examples of the preferred nonionic surfactants include, but are not limited to, $C_8$–$C_{16}$ alkyl ethoxylates with two to seven ethoxylates, available commercially under trade names NEODOL 91-2.5E, NEODOL 91-5E, NEODOL 91-6E, NEODOL 91-8E, NEODOL 23-1.1E, NEODOL 23-2E, NEODOL 23-3E, NEODOL 23-6.5E, NEODOL 25-2.5E, NEODOL 25-3E, NEODOL 25-7E, NEODOL 25-9E, NEODOL 45-4E, and NEODOL 45-7E from Shell Chemical Company, Houston, Tex. Another specific example of a preferred nonionic surfactant includes, but is not limited to wherein the surfactant is a $C_{12}$ ethoxylate with 2–4 ethoxylates.

An example of a preferred anionic surfactant includes, but is not limited to, alkyl and dialkyl sulfocuccinates such as sodium bis(2-ethylhexyl) sulfosuccinate, available commercially under trade name Aerosol OT from Mona Industries.

Gemini surfactants are made up of two long hydrocarbon chains ($C_{12}$–$C_{22}$) and two ionic head groups linked by a short spacer. The spacer is attached directly to the identical ionic groups, each of which is in turn bonded to an identical hydrocarbon chain. The spacer can vary in length, hydrophobicity and flexibility and is typical a $C_2$–$C_5$ divalent alkyl radical. A typical gemini surfactant is as follows:

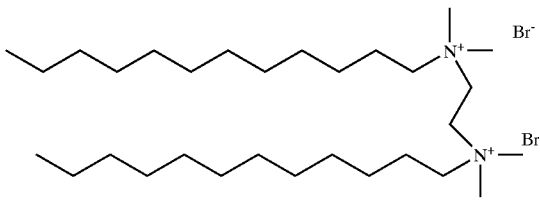

Gemini surfactants are also described further in the book: Surfactants and Polymers in Aqueous Solution, by Bo Jonsson, Bjorn Lindman, Krister Holmberg and Bengt Kronberg, pages 4–5, John Wiley and Sons, copyright 1998.

The surfactant(s) may be present in the composition in a total amount of from about 1 to 50% by weight, preferably from 2 to 40% by weight, more preferably from 5 to 30% by weight.

The liquid emulsifiable concentrates of the present invention may be comprised of one or more differing surfactants or lipid surfactants of the same or differing classes.

Dispersing Aids

The emulsifiable concentrates of the present invention will preferably comprise one or more dispersing aids. Dispersing aides facilitate in the migration of water immiscible solvent into the aqueous phase and thereby improve the self and/or spontaneous emulsification.

Preferred dispersing aides include, but are not limited to, medium-chain alcohols with $C_5$–$C_{10}$ chain lengths including pentanol, hexanol, heptanol, octanol, nonanol, and decanol. Especially preferred medium-chain alcohols include heptanol and octanol. Medium-chain alcohols may be used within the liquid emulsifiable concentrates of the present invention from about 0.5% to 20%, preferably from about 1% to 15%, and more preferably from about 2% to 10%.

Another dispersing aide which may be included within compositions of the present invention is fumed silica. Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates, precipitated silicas and silica gels are generally made in aqueous solution. See, Cabot Technical Data Pamphlet TD-100 entitled "CAB-O-SIL-.RTM. Untreated Fumed Silica Properties and Functions", October 1993, and Cabot Technical Dat Pamphlet TD-104 entitled "CAB-O-SIL.RTM. Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m/gram, most preferably greater than about 180 sq. m./gram. Fumed silica may be used within the liquid emulsifiable concentrates of the present invention at from about 0.1% to 20% and preferably from 0.5% to 15%.

Although the exact mechanism for dispersing aides is not known, it is believed that by partitioning from the oil to the water phase they induce additional interfacial turbulence and thereby enhance self emulsification.

Optional Components

The liquid emulsifiable concentrates of the present invention may include optional benefit materials and cosmetic adjuncts, as long as the benefit materials or the adjuncts do not eliminate or substantially reduce the performance or chemical shelf stability of the reactive agent. The additional ingredients may include, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, dyes, dyes and coloring agents, pearlescents, opacifiers, enzymes, suspending agents, antimicrobials, preservatives, proteins, herb and plant extracts, bleach, peroxide, polyols, silicones, oils, antibodies, pH adjusting agents including pH buffers (to adjust pH upon dilution with the separate aqueous composition), viscosity modifiers, preservatives, viscosity enhancers, gelling agents, chelators, silicones, emulsifying agents, moisturizing and conditioning agents, and other common adjuvants well known to those skilled in the art.

An antioxidant may also be incorporated within the composition. Suitable antioxidants include vitamin E and its derivatives, BHT and BHA.

The composition of the present invention may optionally contain from about 0.1% to about 10%, preferably from about 0.25% to about 8%, more preferably from about 0.5% to about 5% of a stabilizer.

In one embodiment of the present invention, the stabilizer can comprise a crystalline, hydroxyl-containing stabilizer. The crystalline, hydroxy-containing stabilizer is selected from the group consisting of:

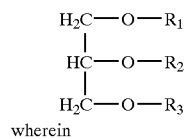

(i)

wherein $R_1$ is

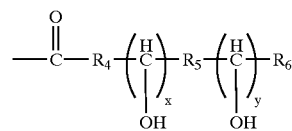

$R_2$ is $R_1$ or H
$R_3$ is $R_1$ or H
$R_4$ is $C_{0-20}$ Alkyl
$R_5$ is $C_{0-20}$ Alkyl
$R_6$ is $C_{0-20}$ Alkyl
$R_4+R_5+R_6=C_{0-22}$
and wherein $1 \leq x+y \leq 4$;

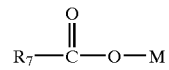

(ii)

wherein $R_7$ is $-R_4(CHOH)_xR_5(CHOH)_yR_6$
M is $Na^+$, $K^+$ or $Mg_{++}$, or H; and
iii) mixtures thereof;

Some preferred hydroxyl-containing stabilizers include 12-hydroxystearic acid, 9,10-dihydroxystearic acid, tri-9,10-dihydroxystearin and tri-12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the personal cleansing compositions herein, they are typically present at from about 0.5% to 10%, preferably from 0.75% to 8%, more preferably from 1.25% to about 5% of the treatment compositions. The stabilizer is insoluble in water under ambient to near ambient conditions.

Alternatively, the stabilizer employed can comprise a polymeric thickener. When polymeric thickeners as the stabilizer in the personal cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic cationic and nonionichomopolymers derived from acrylic and/or methacrylic acid, anionic cationic and nonionic cellulose resins, cationic copolymers of dimethyldialkylammonium chloride and acrylic acid, cationic homopolymers of dimethylalkyl-ammonium chloride, cationic polyalkylene and ethoxypolyalkylene imines, polyethylene glycol of molecular weight from 100,000 to 4,000,000, and mixtures thereof. Preferably, the polymer is selected from the group consisting of Sodium Polyacrylate, hydroxy ethyl Cellulose, Cetyl Hydroxy Ethyl Cellulose, and Polyquaternium 10.

The polymeric thickener is preferably and anionic, nonionic, cationic or hydrophobically modified polymer of natural, modified natural or synthetic origin from plants, microbials, animals or petroleum raw materials including karaya gum, tragacanth gum, gum arabic, gum ghatti, guar gum, locust bean gum, quince seed, psyllium seed, tamarind seed, carrageenan, alginates, agar, larch gum, pectins, starches, xanthan gum, dextran, casein, gelatin, keratin, shellac, cellulose derivatives, guar derivatives, acrylic acid polymers, polyacrylamides, and alkylene/alkylene oxide polymers. Preferred polymeric thickeners include guar gum, available commercially as SUPERCOL U, U NF, SUPERCOL GF, SUPERCOL G2S, and SUPERCOL G3 NF from Aqualon and JAGUAR GUM from Rhone-Poulenc; xanthan gum, available commercially as KELTROL CG, KELTROL CG F, KELTROL CG T, KELTROL CG TF, KELTROL CG 1000, KELTROL CG RD, KELTROL CG GM, KELTROL CG SF, from Calgon, and RHODICARE S, RHODICARE XC, RHODICARE H, AND RHODICARE D, from Rhone-Poulenc; hydroxyethylcellulose, available commercially as NATRASOL 210 types and NATRASOL 250 types from Aqualon; hydroxypropyl guar, available commercially as JAGUAR HP-8, JAGUAR HP-11, JAGUAR HP-60, and JAGUAR H-79 from Rhone-Poulenc. Additional specific polymeric thickeners that are suitable for the present invention are given in *Rheological Properties of Cosmetics and Toiletries*, edited by Dennis Laba, 1993, by Marcel Dekker, Inc. on pages 57 through 121 (ISBN 0-8247-9090-1).

Alternatively, the stabilizer employed can comprise $C_{10}$–$C_{22}$ ethylene glycol fatty acid esters. $C_{10}$–$C_{22}$ ethylene glycol fatty acid esters can also desirably be employed in combination with the polymeric thickeners hereinbefore described. The ester is preferably a diester, more preferably a $C_{14}$–$C_{18}$ diester, most preferably ethylene glycol distearate. When $C_{10}$–$C_{22}$ ethylene glycol fatty acid esters are utilized as the stabilizer in the personal cleansing compositions herein, they are typically present at from about 3% to about 10%, preferably from about 5% to about 8%, more preferably from about 6% to about 8% of the treatment compositions.

Another class of stabilizer which can be employed is dispersed amorphous silica. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates, precipitated silicas and silica gels are generally made in aqueous solution. See, Cabot Technical Data Pamphlet TD-100 entitled "CAB-O-SIL.RTM. Untreated Fumed Silica Properties and Functions", October 1993, and Cabot Technical Dat Pamphlet TD-104 entitled "CAB-O-SIL.RTM. Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the compositions at levels ranging from about 0.1% to about 10%, preferably from about 0.25% to about 8%, more preferably from about 0.5% to about 5%.

A fourth class of stabilizer which can be employed comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and fluorine. See Merck Index, eleventh Edition, 1989, entry 4538, p. 729, which is herein incorporated by reference. When smectite clay is employed as the stabilizer in the treatment compositions of the present invention, it is typically included in amounts ranging from about 0.1% to about 10%, preferably from about 0.25% to about 8%, more preferably from about 0.5% to about 5%.

Aqueous organic solvents may also be included, provided that they do not destabilize the bi-layers.

For use, the composition may be provided at a pH from about 3 to 11, preferably from 4 to 10.

Making

Numerous techniques can be employed to produce the liquid emulsifiable concentrates of the present invention. In general these techniques involve mixing the components that form the liquid emulsifiable concentrate, as well as any additional components, under conditions that permit the formation of the liquid emulsifiable concentrate.

The specific method for producing the liquid emulsifiable concentrate is not critical. Generally, the liquid emulsifiable concentrate is formed by dissolving the reactive agent within the water immiscible solvent and adding the surfactant(s), dispersing aides and any optional ingredients followed by either low or high shear mixing. Heat may be applied as appropriate.

Separate Aqueous Composition

The separate aqueous compositions of the present invention may be provided in any suitable physical form, for example as low to moderate viscosity liquids, lotions, milks, mousses, dispersions, sprays, gels, foams, aerosols, and creams. These separate aqueous compositions may be produced by procedures well known to the skilled artisan. The separate aqueous cosmetic compositions can be used in various manners as other known compositions in the art including but not limited to various rinse-off and leave-on applications such as hair shampoos, skin cleansers, skin lotions, hair conditioners, hair dyes, hair permanent waves, hair straighteners, hair bleaches, styling sprays, hair mousses, two-in-one shampoos, fabric softeners, lotions, nail polishes, hair serums, hair dyes, hair waving, etc.

The separate aqueous compositions of the present invention can be formulated as a fluid, lotion, fluid cream or cream having a viscosity from 500 to 100,000 mPas or above.

The separate aqueous compositions of the present inventions comprise a continuous phase containing water and optional components that are fully soluble within the aqueous continuous phase. In one embodiment, the aqueous phase may comprise conventional hair treatment chemicals including:

hair bleaching agents including, but not limited to, hydrogen peroxide, sodium percarbonate, sodium perborate, magnesium perborate, magnesium dioxide, barium binoxide and combinations thereof;

hair permanent wave agents including, but not limited to, thioglycolic acid, thiolactic acid, cysteine, thioglycerol, thioglycollic hydrazide, thioglycolamide, and glycerol monothioglycollate, salts of hydrogen sulfide, salts of hydrogen cyanide, trihydroxymethyl phosphine or its precursor, tetrahydroxymethyl phosphonium chloride, borohydride, dithionite, hydrosulfite, and sulfoxylate and combinations thereof;

oxidative hair dyes including, but not limited to, p-phenylenediamine, toluene-2,5-diamine, 2-methoxy-p-phenylenediamine, 2-chloro-p-phenylenediamine, toluene-3,4-diamine,o-aminophenol, p-aminophenol, resorcinol, 1-naphthol, pyrogallol, 4-chlororesorcinol, 4-methoxy-m-phenylenediamine, m-phenylenediamine, hydroquinone and mixtures thereof.

semipermanent hair dyes including, but not limited to, 2-nitro-p-phenylenediamine, 4-nitro-o-phenylenediamine, HC red No. 3, HC yellow No. 2, HC yellow No. 4, HC blue No. 1, HC red No. 1, HC orange No. 1, Disperse black 9, Acid orange 3, Disperse violet 1, Disperse blue 1 and mixtures thereof.

hair swelling agents including, but not limited to, urea, thiourea, acetic acid, phosphoric acid, formic acid, formamide, ethyl amine, alkali halides such as potassium iodide, sodium bromide, lithium bromide, and lithium chloride, and mixtures thereof.

The separate aqueous compositions of the present invention may include additional ingredients that are conventionally used within aqueous formulations known to those skilled in the art, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, dyes, dyes and coloring agents, pearlescents, opacifiers, enzymes, suspending agents, antimicrobials, preservatives, proteins, herb and plant extracts, bleach, peroxide, polyols, silicones, oils, antibodies, pH adjusting agents including pH buffers (to adjust pH upon dilution with the separate aqueous composition), viscosity modifiers, preservatives, viscosity enhancers, gelling agents, chelators, silicones, emulsifying agents, moisturizing and conditioning agents, and other common adjuvants well known to those skilled in the art.

The separate aqueous composition may composition contains from about 20% to about 95%, by weight of the composition, of an aqueous continuous phase Product Form The self-emulsifying hair delivery system of the present invention comprises a separately packaged liquid emulsifiable concentrate comprising the reactive agent that is able to self or spontaneously emulsify upon dilution with water, or separate aqueous composition, by the consumer to form an aqueous micro- or macro-emulsion with minimal or no agitation, i.e., self or spontaneous emulsification, either immediately prior to or simultaneous to application to hair. This can be accomplished via employment of a two package or two compartment execution wherein one package or compartment contains the liquid emulsifiable concentrate and the other package or compartment contains the separate aqueous composition. A number of mechanisms can be used to ensure that the two compositions are mixed either immediately prior or during use by the consumer including, but not limited to, i) a dual or multi-chamber package whereby the emulsifiable concentrate is stored within one chamber and the aqueous composition(s) within the other chamber(s) and wherein the contents of all the chambers are intermixed via or after dispensing for use, e.g., dispensing through the same orifice, dispensing through separate orifices followed by mixing within one's hands, dispensing through separate orifices followed by mixing upon application to hair or skin, or combinations thereof ii) multiple packages wherein the emulsifiable concentrate is stored within one of the packages, e.g., bottle, vial, sachet etc., and the separate aqueous composition(s) is stored within a separate package(s), e.g., bottle, vial or sachet, and whereby the volume of one of the packages is sufficiently large enough to enable the addition of the contents of the remaining packages, via pouring, dispensing etc., to enable intermixing of each of the separate compositions prior to use, iii) pouring the contents of both packages or compartments into one's hands which can be mixed by rubbing the hands together or via massaging onto the keratin substrate, and iv) a multichambered package whereby the emulsifiable concentrate is stored within one chamber and the aqueous composition(s) within the other chamber(s) and wherein the chambers are separated by temporary 'barriers' that are removed or compromised prior to use to enable mixing, e.g., deformable barrier(s), breakable of barrier(s), removable barrier(s) etc.

Conversely, the liquid emulsifiable concentrate can be placed within shear sensitive (or other induced release) capsules which are dispersed within the aqueous composition and which rupture (or other induced release) prior or during use.

The present invention may also employ delivery systems as described in U.S. patent application Ser. No. 09/554,701, filed Nov. 20, 1998 (published as WO 99/26596 on Jun. 3, 1999), U.S. patent application Ser. No. 09/554,871, filed Nov. 20, 1998 (published as WO 99/26510 on Jun. 3, 1999), U.S. patent application Ser. No. 09/554,873, filed Nov. 20, 1998 (published as WO 99/26509 on Jun. 3, 1999), U.S. patent application Ser. No. 09/554,872, filed Nov. 20, 1998 (published as WO 99/26511 on Jun. 3, 1999), and U.S. patent application Ser. No. 09/554,697, filed Nov. 18, 1998 (published as WO 99/26508 on Jun. 3, 1999), all of which are herein incorporated by reference.

Method of Use

The compositions of the present invention can be applied to wet hair, partially wet hair or dry hair. The liquid emulsifiable concentrate and separate aqueous composition are intermixed (via packaging dispensing, pouring and shaking, hand rubbing, massaging onto substrate etc.) and applied to the hair with the hands, which may be gloved, and massaged in thoroughly. The contact time between the cosmetic composition of the present invention and the substrate can vary between 10 seconds and about 1 hour, preferably between 20 seconds and 30 minutes, more preferably between 30 seconds and 15 minutes. The composition is then thoroughly rinsed from the hair, though the composition can be applied as a leave-on product.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

All percentages herein are based upon the total weight of the compositions, and all such weight percentages as they pertain to listed ingredients are based on the active level and, therefore, do not include carriers or by-products that may be included in commercially available materials.

Example I

A Non-Limiting Example of a Conditioning Liquid Emulsifiable Concentrate

| Ingredient | A | B | C | D | E |
|---|---|---|---|---|---|
| Polymer 1[1] | 14.40 | 15.68 | 16.34 | 13.84 | 13.84 |
| Isopar C[2] | 70.10 | 76.57 | 79.78 | — | — |
| Neodol 23-3E[3] | 10.00 | 5.00 | 2.50 | 5.00 | 5.00 |
| Heptanol[4] | 5.50 | 2.75 | 1.38 | 2.75 | 2.75 |
| Propylene Carbonate[5] | — | — | — | — | 78.41 |
| Cyclomethicone D5[6] | — | — | — | 78.41 | — |

[1]Polymer 1 is as described herein, the preparation of which can be referenced in pending U.S. application Ser. No. 09/478,855 by R. Glenn et. al, and incorporated by reference.
[2]Available from Exxon
[3]Available from Shell Chemical Company
[4]98 wt % in solution, obtained from Aldrich, item #H280-5
[5]Available from Huntsman
[6]DOW CORNING 245 FLUID from Dow Corning Corporation, Midland, Mich Examples A–E were produced by first dissolving Polymer 1 within the solvent, e.g., isopar C, propylene carbonate or cyclomethicone D5, via stirring for several hours at 50C under closed lid. The neodol 23-3E and heptanol were then added and mixed in for several minutes.

The above exemplary liquid emulsifiable concentrates of the present invention are to be IS inter-mixed with a separate aqueous composition(s) immediately prior or simultaneous to application to the hair substrate. A quantity of the liquid emulsifiable concentrate is added to give 0.25% to 5% by weight of Polymer I of the entire mixture (emulsifiable concentrate +aqueous composition(s)) to be applied to the hair.

For separate aqueous compositions comprising hair bleaching agents, the above exemplary liquid emulsifiable concentrates are mixed with a separate peroxide containing Lotion Developer composition (4–10% hydrogen peroxide), a separate Hair Lightener Base composition (alkalinity) and optionally a Booster Powder composition (accelerator) just prior to application to the hair. As a nonlimiting example, approximately 25–50 grams of Liquid Emulsifiable Concentrate Example B is added to 100 grams of a Lotion Developer composition, 50 grams of a Lightener Base composition and then approximately 15 grams of a booster powder. The mixture is shaken for approximately 20–30 seconds, applied directly to the hair and left on the hair for approximately 30 minutes followed by thorough rinsing. For exemplary compositions of the Hair Lightener Base and the Booster Powder composition, please reference *The Chemical and Physical Behavior of Human Hair, Third Edition*, by Clarence Robbins, 1994 by Springer-Verlag New York, Inc. pages 131–133.

For separate aqueous compositions comprising oxidative hair dyes, the above liquid emulsifiable concentrates are mixed with a separate Oxidizer base (comprises peroxide) and a separate Precursor-coupler base composition (comprises dye precursors, dye couplers and alkalinity) immediately prior or simultaneous to application to the hair. As a nonlimiting example, approximately 30–70 grams of Liquid Emulsifiable Concentrate Example B is added to approximately 100 grams of a Oxidizer base and approximately 100 grams of a Precursor-coupler base composition. The mixture is shaken for approximately 20–30 seconds, applied directly to the hair and left on the hair for approximately 30 minutes followed by thorough rinsing. For exemplary compositions of the Precursor-coupler base composition, please reference *The Chemical and Physical Behavior of Human Hair, Third Edition*, by Clarence Robbins, 1994 by Springer-Verlag New York, Inc. pages 247–249.

Example II

A Non-Limiting Example of a Conditioning Liquid Emulsifiable Concentrate

| Ingredient | A | B | C | D | E |
|---|---|---|---|---|---|
| Polymer II | 14.40 | 15.68 | 16.34 | 13.84 | 13.84 |
| Isopar C[1] | 70.10 | 76.57 | 79.78 | — | — |
| Neodol 23-3E[2] | 10.00 | 5.00 | 2.50 | 5.00 | 5.00 |
| Heptanol[3] | 5.50 | 2.75 | 1.38 | 2.75 | 2.75 |
| Propylene Carbonate[4] | — | — | — | — | 78.41 |
| Cyclomethicone D5[5] | — | — | — | 78.41 | — |

[1]Available from Exxon
[2]Available from Shell Chemical Company
[3]98 wt % in solution, obtained from Aldrich, item #H280-5
[4]Available from Huntsman
[5]DOW CORNING 245 FLUID from Dow Corning Corporation, Midland, Mich Examples A–E were produced by first dissolving Polymer II within the solvent, e.g., isopar C, propylene carbonate or cyclomethicone D5, via stirring for several hours at 50C under closed lid. The neodol 23-3E and heptanol were then added and mixed in for several minutes.

The above exemplary liquid emulsifiable concentrates of the present invention are to be inter-mixed with a separate aqueous composition(s) immediately prior or simultaneous to application to the hair substrate. A quantity of the liquid emulsifiable concentrate is added to give 0.25% to 5% by weight of Polymer I of the entire mixture (emulsifiable concentrate +aqueous composition(s)) to be applied to the hair.

For separate aqueous compositions comprising hair bleaching agents, the above exemplary liquid emulsifiable concentrates are mixed with a separate peroxide containing Lotion Developer composition (4–10% hydrogen peroxide), a separate Hair Lightener Base composition (alkalinity) and optionally a Booster Powder composition (accelerator) just prior to application to the hair. As a nonlimiting example, approximately 25–50 grams of Liquid Emulsifiable Concentrate Example B is added to 100 grams of a Lotion Developer composition, 50 grams of a Lightener Base composition and then approximately 15 grams of a booster powder. The mixture is shaken for approximately 20–30 seconds, applied directly to the hair and left on the hair for approximately 30 minutes followed by thorough rinsing. For exemplary compositions of the Hair Lightener Base and the Booster Powder composition, please reference *The Chemical and Physical Behavior of Human Hair, Third Edition*, by Clarence Robbins, 1994 by Springer-Verlag New York, Inc. pages 131–133.

For separate aqueous compositions comprising oxidative hair dyes, the above liquid emulsifiable concentrates are mixed with a separate Oxidizer base (comprises peroxide) and a separate Precursor-coupler base composition (comprises dye precursors, dye couplers and alkalinity) immediately prior or simultaneous to application to the hair. As a nonlimiting example, approximately 30–70 grams of Liquid Emulsifiable Concentrate Example B is added to approximately 100 grams of a Oxidizer base and approximately 100 grams of a Precursor-coupler base composition. The mixture is shaken for approximately 20–30 seconds, applied directly to the hair and left on the hair for approximately 30 minutes followed by thorough rinsing. For exemplary compositions of the Precursor-coupler base composition, please reference *The Chemical and Physical Behavior of Human Hair, Third Edition*, by Clarence Robbins, 1994 by Springer-Verlag New York, Inc. pages 247–249.

Example III

A Non-Limiting Example of a Conditioning Liquid Emulsifiable Concentrate

| Ingredient | A | B | C | D | E |
|---|---|---|---|---|---|
| Conditioner III | 14.40 | 15.68 | 16.34 | 13.84 | 13.84 |
| Isopar C[1] | 70.10 | 76.57 | 79.78 | — | — |
| Neodol 23-3E[2] | 10.00 | 5.00 | 2.50 | 5.00 | 5.00 |
| Heptanol[3] | 5.50 | 2.75 | 1.38 | 2.75 | 2.75 |
| Propylene Carbonate[4] | — | — | — | — | 78.41 |
| Cyclomethicone D5[5] | — | — | — | 78.41 | — |

[1] Available from Exxon
[2] Available from Shell Chemical Company
[3] 98 wt % in solution, obtained from Aldrich, item #H280-5
[4] Available from Huntsman
[5] DOW CORNING 245 FLUID from Dow Corning Corporation, Midland, Mich Examples A–E were produced by first dissolving Polymer 1 within the solvent, e.g., isopar C, propylene carbonate or cyclomethicone D5, via stirring for several hours at 50C under closed lid. The neodol 23-3E and heptanol were then added and mixed in for several minutes.

The above exemplary liquid emulsifiable concentrates of the present invention are to be inter-mixed with a separate aqueous composition(s) immediately prior or simultaneous to application to the hair substrate. A quantity of the liquid emulsifiable concentrate is added to give 0.25% to 5% by weight of Polymer I of the entire mixture (emulsifiable concentrate +aqueous composition(s)) to be applied to the hair.

For separate aqueous compositions comprising hair bleaching agents, the above exemplary liquid emulsifiable concentrates are mixed with a separate peroxide containing Lotion Developer composition (4–10% hydrogen peroxide), a separate Hair Lightener Base composition (alkalinity) and optionally a Booster Powder composition (accelerator) just prior to application to the hair. As a nonlimiting example, approximately 25–50 grams of Liquid Emulsifiable Concentrate Example B is added to 100 grams of a Lotion Developer composition, 50 grams of a Lightener Base composition and then approximately 15 grams of a booster powder. The mixture is shaken for approximately 20–30 seconds, applied directly to the hair and left on the hair for approximately 30 minutes followed by thorough rinsing. For exemplary compositions of the Hair Lightener Base and the Booster Powder composition, please reference *The Chemical and Physical Behavior of Human Hair, Third Edition*, by Clarence Robbins, 1994 by Springer-Verlag New York, Inc. pages 131–133.

For separate aqueous compositions comprising oxidative hair dyes, the above liquid emulsifiable concentrates are mixed with a separate Oxidizer base (comprises peroxide) and a separate Precursor-coupler base composition (comprises dye precursors, dye couplers and alkalinity) immediately prior or simultaneous to application to the hair. As a nonlimiting example, approximately 30–70 grams of Liquid Emulsifiable Concentrate Example B is added to approximately 100 grams of a Oxidizer base and approximately 100 grams of a Precursor-coupler base composition. The mixture is shaken for approximately 20–30 seconds, applied directly to the hair and left on the hair for approximately 30 minutes followed by thorough rinsing. For exemplary compositions of the Precursor-coupler base composition, please reference *The Chemical and Physical Behavior of Human Hair, Third Edition*, by Clarence Robbins, 1994 by Springer-Verlag New York, Inc. pages 247–249.

What is claimed is:

1. A treatment composition comprising an anhydrous liquid emulsifiable concentrate of a reactive agent comprising, by weight:
    i) from about 0.01% to about 20% of one or more reactive agents wherein the reactive agent is comprised of one or more reactive groups of the electrophilic, nucleophilic or protected thiol type;
    ii) from about 20% to about 99% of a water immiscible solvent;
    iii) from about 2 to about 40% of a surfactant selected from one or more of a $C_8$–$C_{16}$ alkyl ethoxylate with two to seven ethoxylates; and
    iv) from about 0.5% to about 20% of a dispersing aide selected from one or more of a $C_5$–$C_{10}$ alcohol
wherein the anhydrous liquid emulsifiable concentrate of a reactive agent self emulsifies or spontaneously emulsifies upon dilution with water or a separate aqueous composition, to form an aqueous micro- or macro-emulsion either immediately prior to or simultaneous to application to a substrate.

2. A treatment composition according to claim 1, wherein the reactive agent is covalently reactive with an amino acid based substrate.

3. A treatment composition according to claim 2, wherein the reactive agent is covalently reactive with hair.

4. A treatment composition according to claim 3, wherein the reactive agent additionally comprises a cosmetically active functional group.

5. A treatment composition according to claim 3, wherein the reactive agent comprises an electrophilic reactive group selected from the group consisting of halotriazines, haloquinoxalines, halopyrimidines, vinylsulfones, β-haloethylsulfones, β-sulfatoethylsulfones, acrylates, methacrylates, acrylamides, methacrylamides, maleimides, epoxides, acylhalides, esters, carbamates, dithiocarboxylic acid esters, alkoxysilanes, thiosulfates, anhydrides, urea derivatives, isothiocyanates, isocyanates, lactones, thiosulfates, isothiuroniums, azalactones and mixtures thereof.

6. A treatment composition according to claim 3, wherein the reactive agent comprises a nucleophilic reactive group selected from the group consisting of thiols, thiolates, thiols or thiolates containing quaternary salts, thioalkyl esters, thioalkylamides, thiol or thiolate derivatives of cysteamine, and mixtures thereof.

7. A treatment composition according to claim 3, wherein the reactive agent comprises a protected thiol reactive group having the formula $$R—(S—Pr)_m$$

where R is a mono or multivalent cosmetically active functional group, S is sulfur, Pr is a protecting group and m is an integer between 1 and 100.

8. A treatment composition according to claim 7, wherein the protecting group is selected from the group consisting of heterocyclic protecting groups, $sp^2$ aliphatic trigonal carbon protecting groups, $sp^3$ carbon electrophilic protecting groups, phosphorus protecting groups, metal based protecting groups, non-metal and metalloid based protecting groups other than phosphorus, energy-sensitive protecting groups and mixtures thereof.

9. A treatment composition according to claim 1, wherein the water immiscible solvent is selected from the group consisting of a volatile or nonvolatile silicone compound, a volatile or nonvolatile hydrocarbon compound, propylene carbonate and mixtures thereof.

10. A treatment composition according to claim 9, wherein the water immiscible solvent is selected from the group consisting of volatile and nonvolatile hydrocarbon compounds having about 10 to 30 carbon atoms, isododecane, isohexadecane and compounds depicted by the following general structure:

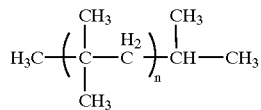

wherein n ranges from 2 to 5.

11. A treatment composition according to claim 9, wherein the water immiscible solvent is selected from the group consisting of linear polydimethylsiloxanes, cyclic polydimethylsiloxanes and mixtures thereof.

12. A treatment composition according to claim 11, wherein the water immiscible solvent is selected from the group consisting of hexamethylsiloxane, cyclomethicone and mixtures thereof.

13. A treatment composition according to claim 1, wherein the surfactant is a $C_{12}$ ethoxylate with 2–4 ethoxylates.

14. A treatment composition according to claim 1, wherein the surfactant is from about 4% to about 15%.

15. A treatment composition according to claim 1, wherein the treatment composition is in the presence of a separate aqueous composition which is comprised of a fluid, lotion, fluid cream or cream having a viscosity from 500 to 100,000 mPas or above.

16. A treatment composition according to claim 15, wherein the separate aqueous composition is a hair shampoo, skin cleanser, skin lotion, hair conditioner, hair dye, hair permanent wave, hair straightener, hair bleach, styling spray, hair mousse, two-in-one shampoo, fabric softener, lotions, nail polish, or hair serum.

17. A method of treating amino acid based substrates by applying to the substrates an effective amount of composition according to claim 1, wherein the composition provides a long-lasting treatment effect.

18. A method of bleaching, coloring, end/or conditioning hair by applying to hair an effective amount of composition according to claim 1, wherein the composition provides a long-lasting treatment effect.

* * * * *